(12) United States Patent
Walzer et al.

(10) Patent No.: US 8,912,359 B2
(45) Date of Patent: Dec. 16, 2014

(54) BISBENZAMIDINES FOR THE TREATMENT OF PNEUMONIA

(75) Inventors: Peter D. Walzer, Loveland, OH (US); Melanie T. Cushion, Miami Township, OH (US); Annie Mayence, Mons (BE); Tien Liang Huang, Metairie, LA (US); Jean Jacques Vanden Eynde, Mons (BE)

(73) Assignees: University of Cincinnati, Cincinnati, OH (US); Xavier University, New Orleans, LA (US)

( * ) Notice: Subject to any disclaimer, the term of this patent is extended or adjusted under 35 U.S.C. 154(b) by 673 days.

(21) Appl. No.: 13/050,169

(22) Filed: Mar. 17, 2011

(65) Prior Publication Data

US 2011/0223238 A1 Sep. 15, 2011

Related U.S. Application Data

(62) Division of application No. 10/595,999, filed as application No. PCT/IB2004/004468 on Nov. 24, 2004, now abandoned.

(60) Provisional application No. 60/525,089, filed on Nov. 25, 2003.

(51) Int. Cl.
| | | |
|---|---|---|
| C07C 239/00 | (2006.01) | |
| A61K 31/7056 | (2006.01) | |
| A61K 31/56 | (2006.01) | |
| C07C 257/18 | (2006.01) | |
| A61K 45/06 | (2006.01) | |
| C07C 259/18 | (2006.01) | |
| A61K 31/167 | (2006.01) | |

(52) U.S. Cl.
CPC ............ *A61K 31/167* (2013.01); *A61K 31/7056* (2013.01); *A61K 31/56* (2013.01); *C07C 257/18* (2013.01); *A61K 45/06* (2013.01); *C07C 259/18* (2013.01); *C07C 2101/02* (2013.01)
USPC .......................................................... 564/157

(58) Field of Classification Search
USPC .......................................................... 564/157
See application file for complete search history.

(56) References Cited

U.S. PATENT DOCUMENTS

2005/0113424 A1 5/2005 Hayashi et al.

FOREIGN PATENT DOCUMENTS

| DE | 1205974 B | * 11/1965 | |
|---|---|---|---|
| WO | WO 2005/033065 | | 4/2005 |

OTHER PUBLICATIONS

Bin Tao et al, "Synthesis and anti-pneumocystis carinii activity of conformationally restricted analogues of pentamidine" European Journal of Medicinal Chemistry (1998) pp. 531-538.*
Vanden Eydne et al. "Novel bisbenzamidines as potential drug candidates for the treatment of Pneumocystis carinii pneumonia" Bioorganic & Medicinal Chemistry Letters (2004), 14(17), 4545-4548.*
Vanden Eynde, J. J. et al., "Novel bisbenzamidines as potential drug candidates for the treatment of Pneumocystis carinii pneumonia," Bioorganic & Medicinal Chemistry Letters, vol. 14(17) (Sep. 6, 2004) pp. 4545-4548, XP002374421 ISSN: 0960-894X.
Tao, B. et al, "Synthesis and anti-Pneumocystis carinii activity of conformationally restricted analogues of pentamidine," European Journal of Medicinal Chemistry, vol. 34(6) (Jun. 1999) pp. 531-538, XP002374422 ISSN: 0223-5234.
Huang, T. L. et al, "N,N'-Bis(4-(N-alkylamidino)phenyl)homopiperazines as anti-Pneumocystis carinii agents," Bioorganic and Medicinal Chemistry Letters, vol. 11(20) (Oct. 22, 2001) pp. 2679-2681, XP002374423 ISSN: 0960-894X.
Huang, T. L. et al., "Synthesis and anti-Pneumocystis carinii activity of piperidine-linked aromatic diimidazolines," Bioorganic and Medicinal Chemistry Letters, vol. 6(17) (1996) pp. 2087-2090, XP002374424 ISSN: 0960-894X.
Boykin, D. W. et al., "Dicationic diarylfurans as anti-Pneumocystis carinii agents," Journal of Medicinal Chemistry, vol. 38(6) (Mar. 17, 1995) pp. 912-916, XP002374425 ISSN: 0022-2623.
Boykin, D. W. et al., "2,5-bis[4-N-alkylamidino)phenyl]furans as anti-Pneumocystis carinii agents," Journal of Medicinal Chemistry, vol. 41(1) (Jan. 1, 1998), pp. 124-129, XP002374426 ISSN: 0022-2623.
Francesconi, I. et al., "2,4-Diphenyl furan diamidines as novel anti-Pneumocystis carinii pneumonia agents," Journal of Medicinal Chemistry (Jun. 17, 1999), pp. 2260-2265, XP002374427 ISSN: 0022-2623.

(Continued)

*Primary Examiner* — Jeffrey H Murray
*Assistant Examiner* — Oluwafemi Masha
(74) *Attorney, Agent, or Firm* — Frost Brown Todd LLC

(57) ABSTRACT

A method of combating infectious agents, such as *Pneumocystis* pneumonia, and a method of treating a subject in need of such treatment is disclosed. The method comprises administering to the subject a bis-benzamidoxime of formula I wherein the linker is a di-substituted cyclic moiety of any ring size and may contain at least one heteroatom; the aromatic group is 1,2-; 1,3-; or 1,4-disubstituted; R is selected from the group consisting of a hydrogen, a linear or branched alkyl group, containing from 1 to 20 carbon atoms; R' is selected from the group consisting of a hydrogen, a linear or branched alkyl group containing from one to twenty carbon atoms, an aromatic ring, a cycloalkyl group containing three to eight carbon atoms, or a hydroxyl group; alternatively, R and R' may form a cyclic structure that can be fused to another cyclic system; or a pharmaceutically acceptable salt thereof. Pharmaceutical formulations and active compounds useful in the practice of the present invention are also disclosed.

I

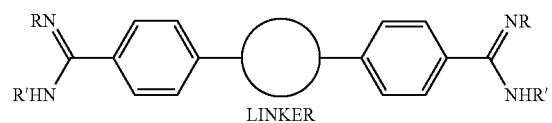

2 Claims, No Drawings

(56) References Cited

OTHER PUBLICATIONS

Mayence, A. et al., "Parallel solution-phase synethesis of conformationally restricted congeners of pentamidine and evaluation of their antiplasmodial activities," Journal of Medicinal Chemistry, vol. 47(10) (May 6, 2004), pp. 2700-2705, XP002374428 ISSN: 0022-2623.

Beard, C. B., et al., "Genetic variation in Pneumocystis carinii isolates from different geographic regions: implications for transmission," Emerg. Infect. Dis., 6(3) (May-Jun. 2000) 265-272.

Castro, M., "Treatment and prophylaxis of Pneumocystis carinii pneumonia," Semin. Respir. Infect. 13. (1998) 296-303.

Centers for Disease Control and Prevention, Surveillance for AIDS-defining opportunistic illnesses 1993-1997. MMWR. Morb. Mortal. Wkly. Rep. 48 No. SS-2 (1999).

Chen, F. et al., "Use of an ATP bioluminescent assay to evaluate viability of Pneumocystis carinii from rats," J.Clin.Microbial, vol. 32 (1994) 2791-2800.

Collins, M. S. et al., "Standardization of an in vitro drug screening assay by use of cryopreserved and characterized Pneumocystis carinii populations," J.Eukaryot.Microbiol. Supp: 178S-179S. (2001) 178S-179S.

Cushion, M. T., et al., "1997). A cytoxicity assay for evaluation of candidate anti-Pneumocystis carinii agents, " Antimicrob.Agents Chemother. 41, (1997) 379-384.

Cushion, M. T., et al., "Effects of atovaquone and diospyrin-based drugs on the cellular ATP of Pneumocystis carinii f sp. Carinii, ".Antimicrob.Agents Chemother. 44 (2000) 713-719.

Cushion, M. T., et al., "Pneumocystis carinii: growth vegetables and estimates in the A549 and WI-38 VA13 human cell lines," Exp. Parasitol. 60 (1985) 43-54.

Cushion, M. T. et al., "Method of testing the susceptibility of Pneumocystis carinii to antimicrobial agents in vitro," Antimicrob. Agents Chemother. 28 (1985) 796-801.

Cushion, M. T. et al., "Cultivation of Pneumocystis carinii in lung-derived cell lines," J.Infect.Dis. 149 (1984a) 644.

Cushion, M. T. et al, "Growth and serial passage of Pneumocystis carinii in the A549 cell line," Infect.Immun. 44 (1984b) 245-251.

Frenkel, J. K. et al., "Latent Pneumocystis infection of rats, relapse, and chemotherapy," Lab.Invest. 15 (1966) 1559-1577.

Hughes, W. T. et al., "Efficacy of a hydroxynaphthoquinone, 566C80, in experimental Pneumocystis carinii pneumonitis," Antimicrob. Agents Chemother. 34(1990) 225-228.

Kaneshiro, E. S. et al., "Effects of sterol inhibitors on the ATP content of Pneumocystis carinii," J.Eukaryot.Microbiol. 45 (1999) 142S-143S.

Kazanjian, P. et al., "Pneumocystis carinii mutations are associated with duration of sulfa or sulfone prophylaxis exposure in AIDS patients," J. Infect. Dis., 2:182 (Aug. 2000) 551-557.

Kazanjian, P. et al., "Pneumocystis carinii cytochrome b mutations are associated with atovaquone exposure in patients with AIDS," J. Infect. Dis., 183(5) (Mar. 1, 2001).

Kazanjian, P. et al., "Pneumocystis carinii cytochrome b mutations are associated with atovaquone exposure in patients with AIDS," J. Infect. Dis., 183(5) (Mar. 1, 2001) 819-822.

Ma, L. et al., "Pneumocystis carinii dihydropteroate synthase but not dihydrofolate reductase gene mutations correlate with prior trimethoprimsulfamethoxazole or dapsone use," J. Infect. Dis. 180 (1999) 1969-1978.

Mei, Q. et al., "Failure of co-trimoxazole in Pneumocystis carinii infection and mutations in dihydropteroate synthase gene," Lancet 351 (1998) 1631-1632.

Mills, J. et al., "Dapsone treatment of Pneumocystis carinii pneumonia in the acquired immunodeficiency syndrome," Antimicrob. Agents Chemother. 32 (1998) 1057-1060.

Walker, D. J. et al., "Sequence polymorphisms in the Pneumocystis carinii cytochrome b gene and their association with atovaquone prophylaxis failure," J. Infect. Dis. 178 (1998) 1767-1775.

Walzer, P. D., "Overview of animal models of Pneumocystis carinii pneumonia," J. Protozool. 38 (1991) 122S-123S.

Walzer, P. D. et al., "In vitro and in vivo effects of quinupristin-dalfopristin against Pneumocystis carinii," Antimicrob. Agents Chemother. 45 (2001) 3234-3237.

Walzer, P. D. et al., "Guanylhydrazones in therapy of Pneumocystis carinii pneumonia in immunosuppresed rats," Antimicrob. Agents Chemother. 38 (1994) 2572-2576.

Walzer, P. D. et al., "Activities of antifolate, antiviral, and other drugs in an immunosuppressed rat model of Pneumocystis carinii pneumonia," Antimicrob. Agents Chemother. 36 (1992a) 1935-1942.

Walzer, P. D. et al, "Treatment of experimental pnumocystosis: review of 7 years of experience and development of a new system for classifying antimicrobial drugs," Antimicrob. Agents Chemother. 36 (1992b) 1943-1950.

Walzer, P. D. et al., "Clinically used antimicrobial drugs against experimental pneumocystosis, singly and in combination: analysis of drug interactions and efficacies," Antimicrob. Agents Chemother. 41(1997) 242-250.

Wilkin, A. et al., "Pneumocystis carinii pneumonia: a clinical review," Am. Fam. Physician. 60 (1999) 1699-4.

\* cited by examiner

BISBENZAMIDINES FOR THE TREATMENT OF PNEUMONIA

CROSS REFERENCE TO RELATED APPLICATIONS

This application is a divisional application of U.S. patent application Ser. No. 10/595,999, which claims priority from U.S. provisional patent application Ser. No. 60/525,089, Walzer et al., filed Nov. 25, 2003.

This invention was funded in part by grants from the National Institutes of Health (Grant Numbers IR01 A150450, RO1-HL64570) and NIH Contracts (Numbers AI-75319, AI-25647 and 2S06GM08008) and a VA Merit Review Grant. The Government may have certain rights in the invention.

FIELD OF THE INVENTION

The present invention relates to bisbenzamidines which are useful against essentially any type of infectious agent, including bacteria, viruses, parasites, and fungi and in particular *Pneumocystis*.

BACKGROUND OF THE INVENTION

Pneumonia caused by *Pneumocystis* (PcP) remains a major opportunistic infection associated with AIDS patients, even in the era of Highly Active Anti-Retroviral Therapy (HAART) (Castro, 1998; Centers for Disease Control and Prevention, 1999). In the previous 2 decades, patients with AIDS have been a primary target of PcP, the population in which it remains a leading opportunistic infection. Limited therapeutic choices and adverse reactions to the two standard treatments, trimethoprim-sulfamethoxazole (TMP-SMX) and pentamidine (Mei, Gurunathan et al., 1998), cause the clinical management of this infection to remain problematic. Moreover, side effects in almost half of AIDs patients required switching to a less effective therapy (Wilkin & Feinberg, 1999). Despite the efforts of several in vitro and in vivo screening projects, no better treatment than TMP-SMX for PcP has been identified (Walzer, Foy et al., 1992b; Wilkin & Feinberg, 1999). Strategies to exploit the effective combination of dihydrofolate reductase inhibitor and DHPS inhibitor of the TMP-SMX combination, by substitution of each component (e.g. TMP-dapsone) have not resulted in any therapies with increased efficacy. More recently, mutations in *Pneumocystis* genes which are the targets of TMP-SMX ((Ma, Borio et al., 1999; Mei, Gurunathan, Masur, & Kovacs, 1998)), atovaquone (Walker, Wakefield et al., 1998) and dapsone (Kazanjian, Armstrong et al.; Kazanjian, Armstrong et al.) were similar to those conferring resistance in other organisms such as *Plasmodium falciparum*. Previous therapy with these agents had a strong correlation to presence of the mutation, suggesting a selective mechanism was operational. Moreover, a Pc genotype with double mutations in the DHPS gene replaced the wild type genotype (no mutations) as the predominant type in certain regions of the country (e.g. San Francisco) implying that again, a dominant selection was occurring and these organisms were being transmitted throughout the human population in these regions (Beard, Carter et al.).

The limited repertoire, problems in tolerance, and potential emerging resistance make it necessary to identify new efficacious treatments for PcP. Drug screening and development for anti-PcP agents has taken advantage of available rodent models of PcP and short term in vitro systems. Recombinant proteins have been used in some biochemical assays when the Pc gene was cloned as in the case of dihydrofolate reductase, but this application has been rarely used due to the paucity of Pc gene sequences previously available.

The rodent model of PcP was developed in 1966 (Frenkel, Good et al., 1966) and since then has been used for the general study of these organisms and for drug development. The efficacy of a compound is evaluated by the decrease in organism numbers in the lungs of treated versus non-treated rats or mice. Organisms can be quantified by microscopic counting methods or by estimation of organism burden using a semi-quantitative scoring system.

An ATP assay system (Cushion, Chen et al., 1997; Chen & Cushion, 1994; Collins & Cushion, 2001) was used to evaluate bisbenzamidine analogues as potential therapeutic targets for treatment of pneumonia, particularly that caused by species in the genus *Pneumocystis*. These compounds exhibited activity against *Pneumocystis* with little or no toxicity, in vitro. Development of these compounds could provide new and novel treatment choices for *Pneumocystis* pneumonia.

The ATP system was used to evaluate the activity of pentamidine analogues and to evaluate their toxicity to three human derived cell lines, A549, Hep-G2 and WI-38.

SUMMARY OF THE INVENTION

A series of novel bisbenzamidines linked by either a rigid or a core are described. The Group I and Group II of compounds described by this invention are summarized by the general structural diagram below:

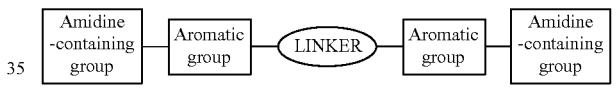

Such compounds may be applicable against essentially any type of infectious agent, including bacteria, viruses, parasites, and fungi.

EXPLANATION OF ACRONYMS

Pc; *Pneumocystis*
PcP; *Pneumocystis* pneumonia
HIV; human immunodeficiency virus
AIDS; Acquired Immune Deficiency Syndrome
$IC_{50}$; Inhibitory concentration 50%
TMP-SMX; trimethoprim sulfamethoxazole
ATP; adenosine triphosphate

DESCRIPTION OF THE INVENTION

A series of novel bisbenzamidines linked by either a rigid (for instance, a phenylene diamide) or a flexible (for instance, a propyl diamide) core are described. Such compounds may be used for the treatment of infections, such as pneumonia and for instance, pneumonia caused by *Pneumocystis*. In vitro evaluation of these compounds using a *Pneumocystis* ATP detection assay indicated that the bisbenzamidines of the present invention functioned as anti-*Pneumocystis* agents.

The Group I and Group II of compounds described by this invention are summarized by the general structural diagram below:

General Structural Diagram:

Group I Compounds

Group I compounds comprise two aromatic groups linked together and having at least one aromatic system bearing an amidine or an amidine-containing group. Examples of Group I compounds include those of the general formulae (and salts thereof) of structure Ia and Ib (below):

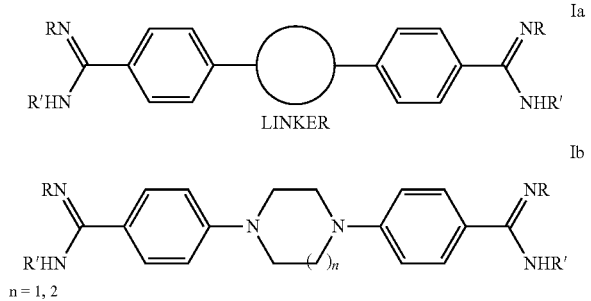

The linker may be any cyclic system of any size and may contain at least one heteroatom. The linker may be aromatic, or, the linker is a 1,4-piperazinediyl group (n=1, Ib) or a 1,4-homopiperazinediyl group (n=2 as shown in structure Ib). The aromatic system is a di-substituted six-membered ring and may contain at least one heteroatom. The aromatic system may also be a fused aryl ring system. The aromatic system is di-substituted, in either the 1,2-; 1,3-; or 1,4-positions.

The R group may be a hydrogen atom or a linear or branched alkyl group, containing from 1 to 20 carbon atoms. R' may be either a hydrogen atom or a linear or branched alkyl group containing from one to twenty carbon atoms or it may be an aromatic ring. When R is a hydrogen atom, R' may be a cycloalkyl group containing three to eight carbon atoms. R and R' may form a cyclic structure that can be fused to another cyclic system. When the substituents R and R' form a cyclic structure, this structure may be aromatic, and it may contain heteroatoms or unsaturated bonds, or, when the substituent R is hydrogen, R' may be a hydroxyl group. In addition, R and R' may contain heteroatoms or unsaturated bonds or other functional groups.

Group II Compounds

Group II compounds comprise two aromatic groups linked together and having at least one di-substituted aromatic system bearing an amidine or an amidine-containing group and also a (de)activating group. These two units are joined by a linking unit of one to twenty carbon atoms. Examples of Group II compounds include those of the general formulae (and salts thereof):

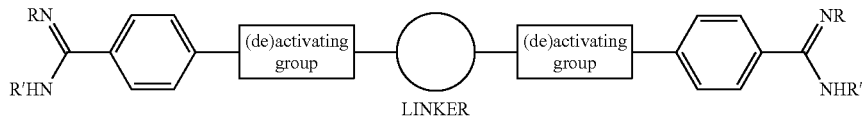

Group II

The linker constitutes a chain of one to twenty carbon atoms, containing saturated and/or unsaturated units, also possibly including a cyclic structure of 1-20 atoms and also possibly containing heteroatoms.

The (de)activating group contains functional groups including but not limited to ether, ester, amide, thioether, thioester, thioamide, amine, or a methylene group.

The aromatic system is di-substituted, six-membered ring and may contain at least one heteroatom. It may also be a fused aryl ring system. The aromatic system is di-substituted in either the 1,2-; 1,3-; or 1,4-positions.

The R group may be a hydrogen atom or a linear or branched alkyl group, containing from 1 to 20 carbon atoms. R' may be either a hydrogen atom or a linear or branched alkyl group containing from one to twenty carbon atoms or an aromatic ring. When R is a hydrogen atom, R' may be a cycloalkyl group containing three to eight carbon atoms, or R and R' may form a cyclic structure that can be fused to another cyclic system. When the substituents R and R' form a cyclic structure, this structure may be aromatic, and it may contain heteroatoms or unsaturated bonds. When R is hydrogen, R' may be a hydroxyl group. In addition, R and R' may contain heteroatoms or unsaturated bonds or other functional groups.

Syntheses

The general strategy used to obtain the derivatives of Group I is shown below (Scheme 1)

Scheme 1:

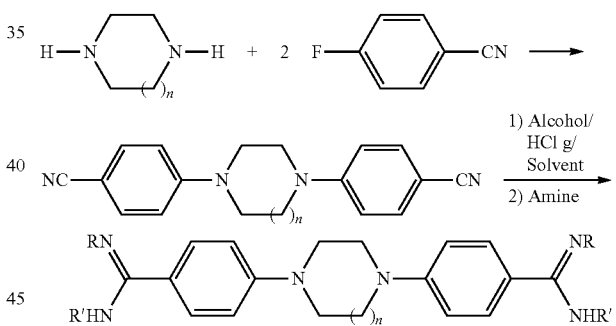

The key step for the preparation of 1,4-diarylpiperazines was a double nucleophilic displacement of fluorine in 4-fluoro derivatives by the nitrogen atoms of piperazine. That reaction, performed in boiling dimethyl formamide, produces the expected tricyclic molecules in good yields, provided the aromatic precursor bears a strong electron-withdrawing group in the para position. Conversion of the bisbenzonitrile derivative into the targeted bisbenzamidines was effected by the Pinner reaction.

The general strategy used to obtain the derivatives of Group II is shown below (Scheme 2).

Scheme 2:

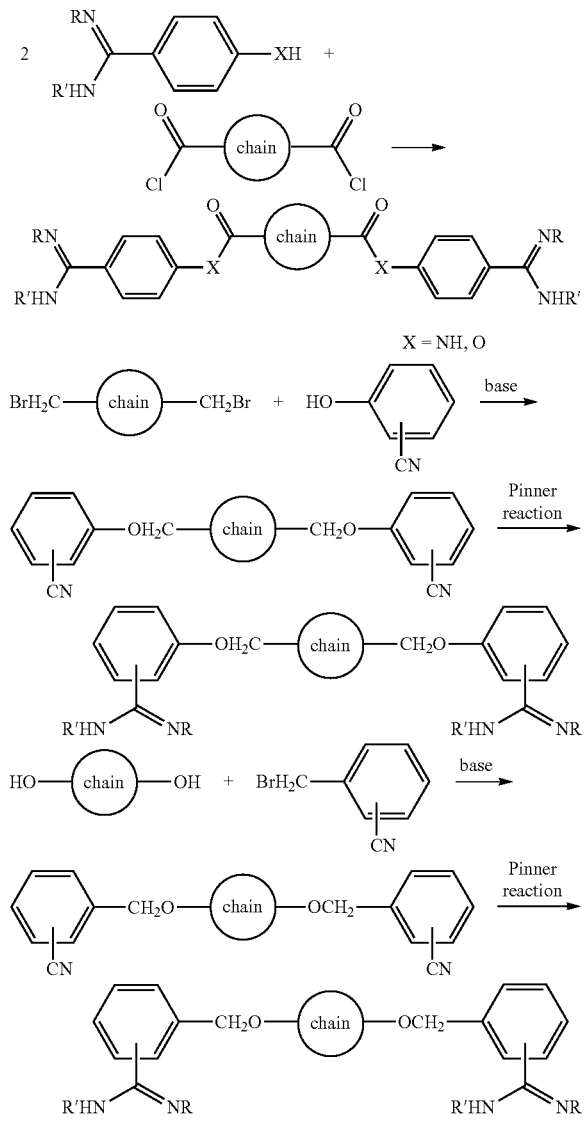

Compounds in which the (de)activating groups are amide or ester groups are obtained from a diacyl chloride and an aminobenzamidine, following classical procedures. Compounds in which the (de)activating groups are methyleneoxy or oxymethylene groups are obtained by a Williamson reaction followed by a Pinner reaction.

General Procedures for Preparation: 4,4'-(1,4-piperazinediyl)bisbenzene-carboximidamides A mixture of 4,4'-(1,4-piperazinediyl)bisbenzonitrile (2 mmol; 0.6 g) in dichloromethane (250 ml) and methanol (10 ml) was saturated with HCl gas, and the reaction medium was left at room temperature for 4 days. The precipitate (crude imidate) was filtered, washed with acetone, and treated with the appropriate amine (20 mmol) in refluxing ethanol (50 ml) for 1 h. After it cooled, the precipitate was filtered and thoroughly washed. When no precipitation occurred, the solution was concentrated under reduced pressure, and the residue was triturated with ether; the solid was filtered and thoroughly washed. Pure analytical samples were obtained without further purification.

4,4'-(1,4-piperazinediyl)bis[N-(2-methylbut-1-yl) benzenecarboximidamide], dihydrochloride salt 1

The overall yield is 55%; melting point (mp) 300° C.; $^1$H NMR (DMSO-d6) δ 9.4 (br s, 2H), 9.2 (br s, 2H), 8.8 (br s, 2H), 7.7 (d, 4H, J=9 Hz), 7.1 (d, 4H, J=9 Hz), 3.5 (s, 8H), 3.4 (m, 4H), 1.8 (m, 2H, J=7 Hz), 1.5 (m, 2H), 1.2 (m, 4H), and 0.8 (m, 12H, J=7 Hz) ppm; IR=3,062, 1,667, 1,606, 1,515, 1,450, and 1,235 cm-$^1$. Anal. Calc. for $C_{28}H_{42}N_{60}$.2 HCl (535.59) C, 62.79; H, 8.28; and N, 15.69. Found: C, 62.52; H, 7.94; and N, 15.49.

4,4'-(1,4-piperazinediyl)bis(N-pentyl benzenecarboximidamide), dihydrochloride salt 2

The overall yield is 45%; mp 300° C.; $^1$H NMR (DMSO-d6) δ 9.5 (br s, 2H), 9.2 (br s, 2H), 8.7 (br s, 2H), 7.7 (d, 4H, J=9 Hz), 7.1 (d, 4H, J=9 Hz), 3.5 (s, 8H), 3.3 (t, 4H, J=7 Hz), 1.6 (m, 4H, J=7 Hz), 1.3 (m, 8H, J=7 Hz), and 0.9 (t, 6H, J=7 Hz) ppm; IR=3,063, 1,672, 1,606, 1,515, 1,396, and 1,235 cm-1. Anal. Calc. for $C_{28}H_{42}N_{60}$.2 HCl (535.59) C, 62.79; H, 8.28; and N, 15.69. Found: C, 62.59; H, 8.44; and N, 15.48.

4,4'-(1,4-piperazinediyl)bis(N-hexyl benzenecarboximidamide), dihydrochloride salt 3

The overall yield is 75%; mp 295 to 297° C.; 1H NMR (DMSO-d6) δ 9.0 (br s, 6H), 7.7 (d, 4H, J_9 Hz), 7.1 (d, 4H, J_9 Hz), 3.5 (s, 8H), 3.4 (t, 4H, J=7 Hz), 1.6 (m, 4H, J=7 Hz), 1.3 (m, 8H), and 0.9 (t, 6H, J=8 Hz) ppm; IR=3,171, 1,674, 1,620, 1,520, 1,394, and 1,166 cm-1. Anal. Calc. for $C_{30}H_{46}N_{60}$.2 HCl.1H$_2$O (581.66) C, 61.95; H, 8.66; and N, 14.45. Found: C, 61.69; H, 8.29; and N, 14.28.

4,4'-(1,4-Piperazinediyl)bis[N-(4-methylbut-1-yl) benzenecarboximidamide], dihydrochloride salt 4

The overall yield is 40%; mp 300° C.; 1H NMR (DMSO-d6) δ 9.4 (br s, 2H), 9.2 (br s, 2H), 8.7 (br s, 2H), 7.7 (d, 4H, J=9 Hz), 7.1 (d, 4H, J=9 Hz), 3.5 (s, 8H), 3.4 (t, 4H), 1.7 (m, 2H), 1.5 (m, 4H, J=7 Hz), and 0.9 (m, 12H, J=7 Hz) ppm; IR_3,093, 1,668, 1,605, 1,515, 1,393, and 1,235 cm_1. Anal. Calc. for $C_{28}H_{42}N_6$.2 HCl (535.59) C, 62.79; H, 8.28; and N, 15.69. Found: C, 62.52; H, 8.37; and N, 15.83.

4,4'-(1,4-piperazinediyl)bis(N-heptylbenzenecarboximidamide), dihydrochloride salt 5

The overall yield is 40%; mp 286° C. (decomp); 1H NMR (DMSO-d6) δ 9.6 (br s, 6H), 7.7 (d, 4H, J=9 Hz), 7.1 (d, 4H, J=9 Hz), 3.5 (s, 8H), 3.4 (t, 4H), 1.6 (m, 4H, J=7 Hz), 1.3 (m, 16H), and 0.8 (t, 6H, J=7 Hz) ppm; IR=3,099, 1,678, 1,608, 1,518, 1,392, and 1,240 cm_1. Anal. Calc. for $C_{32}H_{50}N_6$.2 HCl.1 H$_2$O (609.72) C, 63.03; H, 8.93; N, 13.78. Found: C, 62.59; H, 8.73; and N, 13.66.

4,4'-(1,4-piperazinediyl)bis(N-cyclobutyl benzenecarboximidamide), dihydrochloride salt 6

The overall yield is 25%; mp 300° C.; $^1$H NMR (DMSO-d6) δ 9.6 (br s, 2H), 9.1 (br s, 2H), 8.6 (br s, 2H), 7.7 (d, 4H, J_9 Hz), 7.1 (d, 4H, J_9 Hz), 4.2 (m, 2H, J=8 Hz), 3.5 (s, 8H), 2.4 and 2.2 (2 m, 8H, J=8 Hz), and 1.8 (2 m, 4H, J=8 Hz)

ppm; IR=3,076, 1,667, 1,601, 1,519, and 1,236 cm-1. Anal. Calc. for $C_{26}H_{34}N_6.2HCl$ (503.51) C, 62.02; H, 7.21; and N, 16.69. Found: C, 62.24; H, 7.27; and N, 16.85.

4,4'-(1,4-piperazinediyl)bis(N-cycloheptyl benzenecarboximidamide), dihydrochloride salt 8

The overall yield is 40%; mp 300° C.; $^1$H NMR (DMSO-d6) δ 9.0 (br s, 6H), 7.6 (d, 4H, J=9 Hz), 7.1 (d, 4H, J=9 Hz), 3.9 (m, 2H, J=4 Hz), 3.5 (s, 8H), 1.9 (m, 4H), 1.6-1.5 (m, 12H, J=8 Hz), and 1.4 (m, 8H) ppm; IR=3,062, 1,669, 1,605, 1,516, and 1,230 cm-1. Anal. Calc. for $C_{32}H_{46}N_6.0.2$ HCl (587.67) C, 65.40; H, 8.23; and N, 14.30. Found: C, 65.27; H, 8.04; and N, 14.32.

4,4'-(1,4-piperazinediyl)bis(N-octyl benzenecarboximidamide), dihydrochloride salt 11

The overall yield is: 60%; mp 235° C. (decomp); $^1$H NMR (DMSO-d6) δ 9.0 (br s, 6H), 7.7 (d, 4H, J=9 Hz), 7.1 (d, 4H, J=9 Hz), 3.5 (s, 8H), 3.4 (t, 4H, J=7 Hz) 1.6 (m, 4H, J=7 Hz), 1.3 (m, 20H), and 0.8 (t, 6H, J=7 Hz) ppm; IR 3,107, 1,678, 1,611, 1,518, and 1,394 cm_1. Anal. Calc. for $C_{34}H_{54}N_6.0.2$ HCl.1.5 $H_2O$ (646.78) C, 63.14; H, 9.19; and N, 12.99. Found: C, 62.97; 14, 8.81; and N, 13.11.

4,4'-(1,4-piperazinediyl)bis(N-cyclooctyl benzenecarboximidamide), dihydrochloride salt 12

The overall yield is 45%; mp 300° C.; $^1$H NMR (DMSO-d6) δ 9.0 (br s, 6H), 7.6 (d, 4H, J=9 Hz), 7.1 (d, 4H, J=9 Hz), 3.9 (m, 2H, J=4 Hz), 3.5 (s, 8H), 3.4 (t, 4H, J=7 Hz) 1.7 (m, 12H), and 1.5 (m, 16H) ppm; IR=3,145, 1,661, 1,601, 1,516, and 1,447 cm-1. Anal. Calc. for $C_{34}H_{50}N_6.2$ $HCl.2H_2O$ (651.73) C, 62.66; H, 8.66; and N, 12.90. Found: C, 62.79; H, 8.44; and N, 13.07.

4,4'-(1,4-piperazinediyl)bis(N-nonyl benzenecarboximidamide), dihydrochloride salt 14

The overall yield is 70%; mp 256° C. (decomp); $^1$H NMR (DMSO-d6) δ 8.9 (br s, 6H), 7.7 (d, 4H, J=9 Hz), 7.1 (d, 4H, J=9 Hz), 3.5 (s, 8H), 3.4 (t, 4H, J=7 Hz) 1.6 (m, 4H, J=7 Hz), 1.3 (m, 24H), and 0.8 (t, 6H, J=7 Hz) ppm; IR=3,112, 1,682, 1,614, 1,519, and 1,394 cm_1. Anal. Calc. for $C_{36}H_{58}N_6.0.2$ HCl.1.5 $H_2O$ (674.83) C, 64.07; H, 9.41; and N, 12.45. Found: C, 63.93; H, 9.06; and N, 12.33.

4,4'-(1,4-piperazinediyl)bis(N-dodecyl benzenecarboximidamide), dihydrochloride salt 15

The overall yield is 75%; mp 284° C. (decomp); $^1$H NMR (DMSO-d6) δ 8.6 (br s, 6H), 7.7 (d, 4H, J=9 Hz), 7.1 (d, 4H, J=9 Hz), 3.5 (s, 8H), 3.4 (t, 4H) 1.6 (m, 4H, J=7 Hz), 1.3 (m, 36H), and 0.8 (t, 6H, J=7 Hz) ppm; IR=3,110, 1,679, 1,614, 1,519, and 1,395 cm-1. Anal. Calc. for $C_{42}H_{70}N_6.0.2$ HCl.1 $H_2O$ (749.98) C, 67.26; H, 9.94; and N, 11.20. Found: C, 67.33; H, 9.91; and N, 10.85.

4,4'-(1,4-piperazinediyl)bis(N-ethyl benzenecarboximidamide), dihydrochloride salt 16

The overall yield is 60%; mp 300° C.; $^1$H NMR (DMSO-d6) δ 9.5 (br s, 2H), 9.1 (br s, 2H), 8.7 (br s, 2H), 7.7 (d, 4H, J=9 Hz), 7.1 (d, 4H, J=9 Hz), 3.5 (s, 8H), 3.4 (q, 4H, J=7 Hz), and 1.2 (t, 6H, J=7 Hz) ppm; IR=3,135, 1,667, 1,621, 1,519, and 1,397 cm-1. Anal. Calc. for $C_{22}H_{30}N_6.2$ HCl.0.5 $H_2O$ (460.44) C, 57.39; H, 7.22; and N, 18.25. Found: C, 57.21; H, 7.31; and N, 18.00.

4,4'-(1,4-piperazinediyl)bis(N-decyl benzenecarboximidamide), dihydrochloride salt 18

The overall yield is 50%; mp 271° C. (decomp); $^1$H NMR (DMSO-d6) δ 8.9 (br s, 6H), 7.7 (d, 4H, J=9 Hz), 7.1 (d, 414, J=9 Hz), 3.5 (s, 8H), 3.4 (t, 4H) 1.6 (m, 4H, J=7 Hz), 1.3 (m, 28H), and 0.8 (t, 6H, J=7 Hz) ppm; IR=3,110, 1,679, 1,613, 1,519, and 1,242 cm-1. Anal. Calc. for $C_{38}H_{62}N_6.0.2$ HCl. (675.86) C, 67.53; H, 9.54; and N, 12.43. Found: C, 67.73; H, 9.46; and N, 12.18.

Methods of Treatment

"Dosage form" is intended to mean a form of a pharmaceutical composition suitable for administration to man or a domestic animal. Representative dosage forms include solids and liquids, e.g., perenteral and injection solutions, powders and granules, emollient creams, syrups and elixirs, nasal and ophthalmic drops, intrabronchial inhalants, timed-release capsules, lozenges, troches, suppositories, dermal patches, impregnated bandages and the like.

"Formulary" is intended to mean an agent added to a pharmaceutical composition comprising a bisbenzamidine compound according to the present invention. Representative examples of formulary agents include additives, stabilizers, carriers, binders, buffers, excipients, emollient water-in-oil and oil-in-water emulsions, disintegrants, lubricating agents, antimicrobial agents, preservative and the like; as disclosed further below.

As used herein, an "immunocompromised subject" is a subject who is incapable of developing or unlikely to develop a robust immune response, usually as a result of disease, malnutrition, or immunosuppressive therapy. An immunocompromised immune system is an immune system that is functioning below normal. Immunocompromised subjects are more susceptible to opportunistic infections, for example viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressives, and those who are receiving chemotherapy for cancer. Immunocompromised individuals also includes subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also may be immunocompromised.

The terms "infective agent" or "infectious agent" refers to a harmful or pathogenic organism, including, but not limited to, bacteria, yeast, viruses, protozoa or parasites. In one embodiment, an infectious agent is opportunistic.

In one embodiment, the infectious agent may be a virus. In one embodiment, examples of infectious virus include: Retroviridae (for example, human immunodeficiency viruses, such as HIV-1 (also referred to as HTLV-III, LAV or HTLV-III/LAV, or HIV-III) and other isolates, such as HIV-LP; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (for example, reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV)-1 and HSV-2, varicella zoster virus, cytomegalovirus (CMV), herpes viruses); Poxyiridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for example, Hepatitis C); Norwalk and related viruses, and astroviruses). In another embodiment, viruses to which the invention is applicable include influenza virus type A, influenza virus type B, influenza virus type C, parainfluenza virus type 1, parainfluenza virus type 2, parainfluenza virus type 3, respiratory syncytial virus, a respiratory coronavirus, or a respiratory adenovirus.

The infectious agent may be a bacterium. Bacteria to which the invention is applicable include *Streptococcus pneumoniae, Haemophilus influenzae, Staphylococcus aureus, klebsiella*, or *legionella*. The infectious agent may be a fungus. Fungi to which the invention is applicable include *Pneumocystis* species, *Coccidioides immitis, Histoplasma capsulatum*, or *Cryptococcus neoformans*.

In one embodiment, the infectious agent may be infectious bacteria. In one embodiment, the bacteria include one or more of *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelii*.

In one embodiment, the infectious agent may be an infectious fungi. In one embodiment, the fungi include, but are not limited to, *Pneumocystis* species, *Cryptococcus neoformans, Histoplasma capsulatum, Coccidioides immitis, Blastomyces dermatitidis, Chlamydia trachomatis*, and *Candida albicans*.

In one embodiment, the infectious agent may be other infectious organisms (such as protists), including *Plasmodium falciparum* and *Toxoplasma gondii*.

In one embodiment, the infectious agent may be a lentivirus. As used herein, a lentivirus is a genus of the family retroviridae consisting of non-oncogenic retroviruses that produce multi-organ diseases characterized by long incubation periods and persistent infection. Lentiviruses are unique in that they contain open reading frames (orfs) between the polymerase (pol) and envelope (env) genes and in the 3' env region. Five serogroups are recognized, reflecting the mammalian hosts with which they are associated. Lentiviruses include, but are not limited to human immunodeficiency virus, type 1 (HIV-1), human immunodeficiency virus, type 2 (HIV-2), simian immunodeficiency virus, agm (SIVagm), simian immunodeficiency virus, mnd (SIVmnd), simian immunodeficiency virus, syk (SIVsyk), simian immunodeficiency virus, col (SIVcol), Visna-Maedi virus (VMV), bovine immunodeficiency virus (BIV), feline immunodeficiency virus (FIV), caprine arthritis-encephalitis virus (CAEV), and equine infectious anemia virus (EIAV).

The present invention covers the treatment of intracellular pulmonary infections that involve uptake and transport by the lung's macrophages in dissemination and persistence. These include but are not limited to, *Bacillus anthracis, Listeria monocytogenes, Staphylococcus aureus, Salmenellolosis, Pseudomonas aeruginosa, Yersina pestis, Mycobacterium leprae, M. africanum, M. asiaticum, M. avium-intracellulare, M. chelonei* subsp. *abscessus, M. fallax, M. fortuitum, M. kansasii, M. leprae, M. malmoense, M. shimoidei, M. simiae, M. szulgai, M. xenopi, M. tuberculosis, Brucella melitensis, Brucella suis, Brucella abortus, Brucella canis, Legionella pneumonophilia, Francisella tularensis, mycoplasma* including *Mycoplasma penetrans* and *Mycoplasma pneumoniae*, bacterial, viral and fungal pneumonia, Hantavirus pulmonary syndrome, Respiratory syncytial virus, influenza.

The term "intracellular infection" is used to describe infection where at least some of the infective agent resides inside a cell of the person or animal infected.

As used herein, an "opportunistic infection" is an infection that occurs in an immunocompromised subject. Opportunistic infections may result from treatments or from alterations in the immune system. The infectious agent can be viral, bacterial, protozoan, or fungal. Opportunistic infections can include, but are not limited to bacterial infections such as salmonellosis, syphilis and neurosyphilis, turberculosis (TB), a typical mycobacterial infection, and bacillary angiomatosis (cat scratch disease), fungal infections such as pneumocystosis (PcP), aspergillosis, candidiasis (thrush, yeast infection), coccidioidomycosis, cryptococcal meningitis, microsporidiosis, and histoplasmosis; protozoal infections such as cryptosporidiosis, isosporiasis, and toxoplasmosis, viral infections such as Cytomegalovirus (CMV), hepatitis, herpes simplex (HSV, genital herpes), herpes zoster (HZV, shingles), human papiloma virus (HPV, genital warts, cervical cancer), Molluscum Contagiosum, oral hairy leukoplakia (OHL), and progressive multifocal leukoencephalopathy (PML), and neoplasms such as Kaposi's sarcoma, systemic non-Hodgkin's lymphoma (NHL), and primary CNS lymphoma, among others.

"Pharmaceutical composition", is intended to mean a composition containing one or more bisbenzamidine compounds according to present invention and a formulary effective to provide a dosage form suitable for administration to man or a domestic animal. Representative examples of formularies and dosage forms so suitable are provided below.

The phrase "pharmaceutically acceptable" refers to molecular entities and compositions that do not produce an allergic or similar untoward reaction when administered to a human. As used herein, "carrier" or "excipient" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

"Subject in need thereof" is intended to mean a mammal, e.g., humans, domestic animals and livestock. Representative examples of subjects in need thereof include humans and domestic animals having an infection. Representative infections include pulmonary infections, nasal infections, bronchial infections, dermal infections, infections of dense tissues, (e.g., muscle, connective tissues, tendons and ligaments), and infections of the peripheral and central nervous system.

The term "treatment" as used herein covers any treatment of a disease in a mammal, particularly a human, and includes: (i) preventing the disease from occurring in a subject which may be predisposed to the disease but has not yet been diagnosed as having it; (ii) inhibiting the disease, i.e., arresting its development; or (iii) relieving the disease, i.e., causing regression of the disease, or otherwise preventing, ameliorating, treating or improving a medical condition.

The present invention broadly concerns prophylactic and therapeutic methods of treating certain diseases and other medical conditions by administration of an effective amount of one or more bisbenzamidine compounds described herein or a pharmaceutical composition comprising one or more such compounds. Thus, in one aspect, the present invention provides methods for treating, ameliorating and/or substantially preventing infectious diseases in eukaryotic subjects, particularly in animals, in one embodiment in humans.

The methods described herein are applicable against essentially any type of infectious agent, including bacteria, viruses, parasites, and fungi. Illustratively, the invention is useful for the prophylactic and/or therapeutic treatment of bacterial infections by species from *Pseudomonas, Escherichia, Klebsiella, Enterobacter, Proteus, Serratia, Candida, Staphylococci, Streptococci, Chlamydia, Mycoplasma* and numerous others. Illustrative viral conditions that may be treated in accordance with the invention include those caused, for example, by Influenza viruses, Adenoviruses, parainfluenza viruses, Rhinoviruses, respiratory syncytial viruses (RSVs), Herpes viruses, Cytomegaloviruses, Hepatitis viruses, e.g., Hepatitis B and C viruses, and others. Illustrative fungi include, for example, *Aspergillis, Candida albicans, Cryptococcus neoformans, Coccidioides immitus*, and others.

In one illustrative embodiment, the invention provides methods for the treatment of subjects, particularly immunocompromised subjects, which have developed or are at risk for developing infections. In a related embodiment, the present invention provides prophylactic treatments for immunocompromised patients, such as HIV-positive patients, who have developed or are at risk for developing pneumonia from either an opportunistic infection or from the reactivation of a suppressed or latent infection.

In another related embodiment, the methods of the present invention are used for treating other patient populations that may be immunocompromised and/or at risk for developing infectious diseases, including, for example, patients with cystic fibrosis, chronic obstructive pulmonary disease and other immunocompromised and/or institutionalized patients.

In support of these and other embodiments of the invention, we have demonstrated that pre-challenge administration of an illustrative compound of the present invention in immunocompromised mice provides significant prophylactic protection against infection by *Pneumocystis*.

In another aspect of the invention, the bisbenzamidine compounds described herein are employed in methods for treating, ameliorating or substantially preventing allergic disorders and conditions, such as sinusitis, chronic rhinosinusitus, asthma, atopic dermatitis and psoriasis.

As noted above, the methods of the present invention are useful for treating *Pneumocystis* pneumonia. The methods of the present invention are useful for treating these conditions in that they inhibit the onset, growth, or spread of the condition, cause regression of the condition, cure the condition, or otherwise improve the general well-being of a subject inflicted with, or at risk of contracting the condition.

Subjects to be treated by the methods of the present invention are typically human subjects, although the methods of the present invention may be useful with any suitable subject known to those skilled in the art.

As noted above, the present invention provides pharmaceutical formulations comprising the aforementioned active compounds, or pharmaceutically acceptable salts thereof, in pharmaceutically acceptable carriers for oral, intravenous, or aerosol administration as discussed in greater detail below.

The therapeutically effective dosage of any specific compound, the use of which is in the scope of present invention, will vary somewhat from compound to compound, patient to patient, and will depend upon the condition of the patient and the route of delivery. As a general proposition, a dosage from about 0.1 to about 100 mg/kg will have therapeutic efficacy, with all weights being calculated based upon the weight of the active base, including the cases where a salt is employed. A dosage from about 10 mg/kg to about 50 mg/kg may be employed for oral administration. The duration of the treatment is usually once per day for a period of two to three weeks or until the *Pneumocystis* pneumonia is essentially controlled. Lower doses given less frequently can be used to prevent or reduce the incidence of recurrence of the infection.

In accordance with the present method, an active compound as described herein, or a pharmaceutically acceptable salt thereof, may be administered orally as a solid or as a liquid, or may be administered intravenously. Alternatively, the active compound or salt may also be administered by inhalation. When administered through inhalation the active compound or salt should be in the form of a plurality of solid particles or droplets having a particle size from about 0.5 to about 5 microns, in one embodiment from about 1 to about 2 microns.

Besides providing a method for treating *Pneumocystis* pneumonia, the active compounds of the present invention also provide a method for prophylaxis against *Pneumocystis* pneumonia in an immunocompromised patient, such as one suffering from AIDS. Accordingly, the present invention provides a method for the prophylaxis against *Pneumocystis* pneumonia comprising administering to the patient a prophylactically effective amount of the active compound or a pharmaceutically acceptable salt thereof. The forms for administration of the compound or salt in accordance with this method may be the same as utilized for the purpose of actually treating a patient suffering from *Pneumocystis* pneumonia.

An additional useful aspect of the present invention is a method for prophylaxis against even an initial episode of *Pneumocystis* pneumonia in an immunocompromised patient who has never experienced an episode of *Pneumocystis* pneumonia. In this respect, a patient who has been diagnosed as being immunocompromised, such as one suffering from AIDS or ARC (AIDS related complex), even before the onset of an initial episode of *Pneumocystis* pneumonia, may avoid or delay suffering from the infection by having administered a prophylactically effective amount of an active compound of the present invention or a pharmaceutically acceptable salt thereof. The compound or salt may be administered in the same fashion as in the treatment of patients suffering from *Pneumocystis* pneumonia.

In the manufacture of a medicament according to the invention (a "formulation"), active agents or the pharmaceutically acceptable salts thereof (the "active compound") are typically admixed with, inter alia, an acceptable carrier. The carrier must, of course, be acceptable in the sense of being compatible with any other ingredients in the formulation and must not be deleterious to the subject. The carrier may be solid or liquid, or both, and is generally formulated with the compound as a unit-dose formulation, for example, a tablet, which may contain from 0.05% to 99% by weight of the active compound. One or more active compounds may be incorporated in the formulations of the invention (e.g. the formulation may contain one or more additional anti-*Pneumocystis* agents as noted above), which formulations may be prepared by any of the well-known techniques if pharmacy consisting essentially of admixing the components, including one or more accessory therapeutic ingredients.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations for oral administration may optionally include enteric coatings known in the art to prevent degradation of the formulation in the stomach and provide release of the drug in the small intestine.

In addition to the active compounds or their salts, the pharmaceutical compositions may contain other additives, such as pH adjusting additives. In particular, useful pH adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Other pharmaceutical compositions may be prepared from the water-insoluble active compounds, or salts thereof, such as aqueous base emulsions. In such an instance, the composition will contain a sufficient amount of pharmaceutically acceptable emulsifying agent to emulsify the desired amount of the active compound or salt thereof. Particularly useful emulsifying agents include phosphatidyl cholines, and lecithin.

Further, the present invention provides liposomal formulations of the active compounds and salts thereof. The technology for forming liposomal suspensions is well known in the art. When the active compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the active compounds or salts thereof, may be lyophilized to produce a lyophilizate which may be reconstituted with a pharmaceutically acceptable carrier, such as water, to regenerate a liposomal suspension. The liposomal formulations may contain one or more additional active compounds.

Pharmaceutical formulations are also provided which are suitable for administration as an aerosol, by inhalation. These formulations comprise a solution or suspension of the desired active compound or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid active compound, or a salt thereof, in any appropriate manner known in the art, such as by micronization. In another embodiment, the size of the solid particles or droplets will be from about 1 to about 2 microns. In this respect, commercial nebulizers are available to achieve this purpose.

In one embodiment, when the pharmaceutical formulation suitable for administration as an aerosol-is in the form of a liquid, the formulation will comprise a water-soluble active compound of the present invention or a salt thereof, in a carrier which comprises water. A surfactant may be present which lowers the surface tension of the formulation sufficiently to result in the formation of droplets within the desired size range when subjected to nebulization.

Formulations of the present invention suitable for intravenous administration comprise sterile aqueous and non-aqueous injection preparations of the active compound, which preparations are generally isotonic with the blood of the intended recipient. These preparations may include anti-oxidants, buffers, bacteriostats, and solutes that render the formulation isotonic with the blood of the intended recipient. Aqueous and non-aqueous sterile suspensions may include suspending agents and thickening agents. The formulations may be presented in unit/dose or multi-dose containers, for example sealed ampules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

As indicated, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

One embodiment of the invention provides a method of treating lower respiratory tract disease in a host, susceptible to or suffering from a lower respiratory tract disease caused by an infectious agent. This method comprises administering to the host an amount of a bisbenzamidine anti-infectious agent with activity against the infectious agent and topically administering to the host an amount of an anti-inflammatory agent effective to produce a therapeutic effect against the disease.

Another embodiment of the invention provides a method of treating lower respiratory tract disease in a host, susceptible to or suffering from a lower respiratory tract disease caused by an infectious agent, comprising topically administering to the host an amount of a bisbenzamidine anti-infectious agent and an anti-inflammatory agent effective to produce a therapeutic effect against the disease. In one embodiment, the anti-inflammatory agent is administered directly into the lower respiratory tract of the host.

The combination of bisbenzamidine anti-infectious agent and an anti-infectious agent may be administered topically, orally, intravenously, or intraperitoneally. In one embodiment, the administration is topical administration.

In one embodiment, the anti-inflammatory agent and the anti-infectious agent are administered directly into the lower respiratory tract of the host. The anti-inflammatory agent and/or the anti-infectious agent may be administered intranasally. The anti-inflammatory agent and/or the anti-infectious agent may be administered intranasally in the form of aerosol particles. In one embodiment, the aerosol particles are liposomal compositions.

In one embodiment, the anti-inflammatory agent may be administered at a dosage of from 0.1 g to 100 mg/kg body weight of the host. In another embodiment, the range for the anti-inflammatory agent is a dosage of from 2 µg to 2 mg/kg body weight of the host.

In one embodiment, the anti-infectious agent may be administered at a dosage of from 0.1 µg to 1000 mg/kg body weight of the host. In another embodiment, the range for the anti-infectious agent is a dosage of from 2 µg to 20 mg/kg body weight of the host.

In one embodiment, the anti-inflammatory agent may be a corticosteroid. Suitable corticosteroids are cortisone, hydrocortisone, triamcinolone, dexamethasone, or beclamethasone. Triamcinolone is used as a corticosteroid in one embodiment.

The corticosteroid may be administered at a dosage of from 0.01 to 1000 mg/kg body weight of the host. In another embodiment, the range for the corticosteroid is a dosage of from 0.5 to 50 mg/kg body weight of the host.

In one embodiment, the anti-inflammatory agent may be indomethacin, ibuprofen, or acetylsalicylic acid. In one embodiment, the anti-inflammatory agent may be an anti-cytokine agent. In one embodiment, the anti-cytokine agent may be a monoclonal or polyclonal antibody directed against a cytokine. The cytokines may be tumor necrosis factor, an interleukin, or an interferon.

In one embodiment, the compositions of the present invention may comprise one or more additional active agents. In one embodiment, the additional active agent is another anti-infectious agent.

The anti-infectious agent may be an antibody to the infectious agent. The antibody may be a polyclonal antibody or monoclonal antibody. The monoclonal antibody may be derived from mouse cells, human cells, or genetically-engineered cells.

The anti-infectious agent may be human immunoglobulin which comprises antibodies to the infectious agent. The antibodies in the human immunoglobulin may be monoclonal, polyclonal, or genetically-engineered antibodies. In one embodiment, the human immunoglobulin is human immunoglobulin G. In another embodiment, the anti-infectious agent is human immunoglobulin G which comprises polyclonal antibodies. The human immunoglobulin G may be administered at a dosage of from 0.1 µg to 100 mg/kg body weight of the host. A dosage for the human immunoglobulin G may be from 0.1 mg to 20 mg/kg body weight of the host.

The human immunoglobulin may be human immunoglobulin A or human immunoglobulin M. In one embodiment, the human immunoglobulin A or M comprise monoclonal antibodies.

In another embodiment, the anti-infectious agent is human immunoglobulin which comprises antibodies to a virus, especially respiratory syncytial virus or parainfluenza virus type 3.

The additional anti-infectious agent may be an anti-bacterial agent such as a macrolide, a penicillin, a cephalosporin, or a tetracycline. The anti-infectious agent may be an antifungal agent such as amphotericin b, fluconazole, or ketoconazole. The anti-infectious agent may be an anti-parasitic agent such as trimethoprim, pentamidine, or a sulfonamide. The anti-infectious agent may be an anti-viral agent such as ribavirin or amantidine.

In one embodiment of the invention provides a method of treating lower respiratory tract disease in a host, susceptible to or suffering from a lower respiratory tract disease caused by a virus, comprising administering to the host an amount of bisbenzamidine with activity against the virus and administering directly to the lower respiratory tract of the host an amount of an anti-inflammatory agent effective to produce a therapeutic effect against the disease. The bisbenzamidine may be administered directly to the lower respiratory tract of the host. The virus may be respiratory syncytial virus or parainfluenza virus type 3. The composition may include an anti-viral agent as an additional active agent. The anti-viral agent may be ribavirin or human immunoglobulin G which comprises antibodies to the virus.

In another embodiment, the invention provides a method of treating lower respiratory tract disease in a human, susceptible to or suffering from a lower respiratory tract disease caused by respiratory syncytial virus or parainfluenza virus type 3, comprising administering directly into the lower respiratory tract of the human an amount of bisbenzamidine, an amount of an anti-inflammatory agent and an amount of human immunoglobulin G effective to produce a therapeutic effect against the disease. The bisbenzamidine, anti-inflammatory agent and the human immunoglobulin G may be administered in the form of aerosol particles. The anti-inflammatory agent may be a corticosteroid. In turn, the corticosteroid may be triamcinolone.

In another embodiment, the invention provides a method of treating lower respiratory tract disease in a host, susceptible to or suffering from a lower respiratory tract disease caused by parainfluenza virus type 3, adenovirus type 5, or respiratory syncytial virus, comprising administering directly into the lower respiratory tract of the host an amount of bisbenzamidine and an anti-inflammatory agent effective to produce a therapeutic effect against the disease.

One embodiment of the invention provides a medication that comprises aerosol particles comprising a bisbenzamidine composition of the present invention and an anti-inflammatory agent. This medication is useful in treating lower respiratory tract disease.

Another embodiment of the invention provides a device that expels aerosol particles. The aerosol particles comprise bisbenzamidine, an anti-infectious agent and an anti-inflammatory agent.

In another embodiment, the present invention concerns pharmaceutical compositions comprising one or more of the bisbenzamidine compounds disclosed herein in pharmaceutically-acceptable carriers/excipients for administration to a cell, tissue, animal or plant, either alone, or in combination with one or more other modalities of therapy. In an embodiment, the pharmaceutical compositions are formulated in the absence of exogenous antigen, i.e., are used in monotherapeutic applications. For many such embodiments, the pharmaceutical compositions of the invention will comprise one or more of the bisbenzamidine compounds described herein.

Illustrative carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

In certain embodiments, the pharmaceutical compositions will comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives.

For certain applications, aqueous formulations will be used, particularly those comprising an effective amount of one or more surfactants. For example, the composition can be in the form of a micellar dispersion comprising at least one suitable surfactant, e.g., a phospholipid surfactant. Illustrative examples of phospholipids include diacyl phosphatidyl glycerols, such as dimyristoyl phosphatidyl glycerol (DPMG), dipalmitoyl phosphatidyl glycerol (DPPG), and distearoyl phosphatidyl glycerol (DSPG), diacyl phosphatidyl cholines, such as dimyristoyl phosphatidylcholine (DPMC), dipalmitoyl phosphatidylcholine (DPPC), and distearoyl phosphatidylcholine (DSPC); diacyl phosphatidic acids, such as dimyristoyl phosphatidic acid (DPMA), dipalmitoyl phosphatidic acid (DPPA), and distearoyl phosphatidic acid (DSPA); and diacyl phosphatidyl ethanolamines such as dimyristoyl phosphatidyl ethanolamine (DPME), dipalmitoyl phosphatidyl ethanolamine (DPPE) and distearoyl phosphatidyl ethanolamine (DSPE). Typically, a surfactant:bisbenzamidine molar ratio in an aqueous formulation will be from about 10:1 to about 1:10, more typically from about 5:1 to about 1:5, however any effective amount of surfactant may be used in an aqueous formulation to best suit the specific objectives of interest.

The compounds and pharmaceutical compositions of the invention can be formulated for essentially any route of administration, e.g., injection, inhalation by oral or intranasal routes, rectal, vaginal or intratracheal instillation, ingestion, or transdermal or transmucosal routes, and the like. In this way, the therapeutic effects attainable by the methods and compositions of the invention can be, for example, systemic, local, tissue-specific, etc., depending of the specific needs of a given application of the invention.

Illustrative formulations can be prepared and administered parenterally, i.e., intraperitoneally, subcutaneously, intramuscularly or intravenously. One illustrative example of a carrier for intravenous use includes a mixture of 10% USP ethanol, 40% USP propylene glycol or polyethylene glycol 600 and the balance USP Water for Injection (WFI). Other illustrative carriers include 10% USP ethanol and USP WFI; 0.01-0.1% triethanolamine in USP WFI; or 0.01-0.2% dipalmitoyl diphosphatidylcholine in USP WFI; and 1-10% squalene or parenteral vegetable oil-in-water emulsion. Pharmaceutically acceptable parenteral solvents will generally be selected such that they provide a solution or dispersion which may be filtered through a 0.22 micron filter without removing the active ingredient.

Illustrative examples of carriers for subcutaneous or intramuscular use include phosphate buffered saline (PBS) solution, 5% dextrose in WFI and 0.01-0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01-0.2% dipalmitoyl diphosphatidylcholine in USP WFI and 1 to 10% squalene or parenteral vegetable oil-in-water emulsions.

Examples of carriers for administration via mucosal surfaces depend upon the particular route, e.g., oral, sublingual, intranasal, etc. When administered orally, illustrative examples include pharmaceutical grades of mannitol, starch, lactose, magnesium stearate, sodium saccharide, cellulose, magnesium carbonate and the like, with mannitol being used in one embodiment. When administered intranasally, illustrative examples include polyethylene glycol, phospholipids, glycols and glycolipids, sucrose, and/or methylcellulose, powder suspensions with or without bulking agents such as lactose and preservatives such as benzalkonium chloride, EDTA. In a particularly illustrative embodiment, the phospholipid 1,2 dipalmitoyl-sn-glycero-3-phosphocholine (DPPC) is used as an isotonic aqueous carrier at about 0.01-0.2% for intranasal administration of the compound of the subject invention at a concentration of about 0.1 to 3.0 mg/ml.

When administered by inhalation, illustrative carriers include polyethylene glycol or glycols, DPPC, methylcellulose, powdered dispersing agents, and preservatives, with polyethylene glycols and DPPC being used in one embodiment. In one embodiments, the active compounds be in a nebulized form when administration by inhalation. Illustratively, delivery may be by use of a single-use delivery device, a mist nebulizer, a breath-activated powder inhaler, an aerosol metered-dose inhaler (MDI) or any other of the numerous nebulizer delivery devices available in the art. Additionally, mist tents or direct administration through endotracheal tubes may also be used. Delivery via an intratracheal or nasopharyngeal mode will be efficacious for certain indications.

It will be understood that, if desired, the compounds disclosed herein may be administered in combination with other therapeutic modalities, such as antimicrobial, antiviral and antifungal compounds or therapies, various DNA-based therapeutics, RNA-based therapeutics, polypeptide-based therapeutics and/or with other immunoeffectors. In fact, essentially any other component may also be included, given that the additional component(s) do not cause a significant adverse effect upon contact with the target cells or host tissues. The compositions may thus be delivered along with various other agents as required or desired for the specific embodiment(s) of the invention being implemented.

Illustratively, the pharmaceutical compositions of the invention can include, or be used in conjunction with, DNA encoding one or more therapeutic proteins, antisense RNAs, ribozymes or the like. The DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). In one embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N.Y Acad. Sci. 569: 86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art.

The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells. It will be apparent that a pharmaceutical composition of the invention may comprise both a polynucleotide and a protein component.

Any of a variety of additional immunostimulants may be included in the compositions of this invention. For example, cytokines, such as GM-CSF, interferons or interleukins to further modulate an immune response of interest. For example, in certain embodiments, additional components may be included in the compositions to further enhance the induction of high levels of Th1-type cytokines (e.g., IFN-γ, TNF-α, IL-2 and IL-12). Alternatively, or in addition, high levels of Th2-type cytokines (e.g., IL-4, IL-5, IL-6 and IL-10) may be desired for certain therapeutic applications. The levels of these cytokines may be readily assessed using standard assays. For a review of the families of cytokines, see Mosmann and Coffman, Ann. Rev. Immunol. 7:145-173, 1989.

Illustrative compositions for use in induction of Th1-type cytokines include, for example, a combination of CpG-containing oligonucleotides (in which the CpG dinucleotide is unmethylated) as described, for example, in WO 96/02555, WO 99/33488 and U.S. Pat. Nos. 6,008,200 and 5,856,462 Immunostimulatory DNA sequences are also described, for example, by Sato et al., Science 273:352, 1996. Other suitable immunostimulants comprise saponins, such as QS21 (Aquila Biopharmaceuticals Inc., Framingham, Mass.), and related saponin deriviatives and mimetics thereof.

Other illustrative immunostimulants that can be used in conjunction with the present invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), and Enhanzyn™ immunostimulant (Corixa, Hamilton, Mont.). Polyoxyethylene ether immunostimulants, are described in WO 99/52549A1.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by addition of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts. Also included within the scope of the invention are the hydrated forms of the compounds which contain various amounts of water, for instance, the hydrate, hemihydrate and sesquihydrate forms.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

In applying the compounds of this invention to treatment of the above conditions, administration of the active compounds and salts described herein can be via any of the accepted modes of administration, including oral, parenteral and otherwise system of route of administration. Any pharmaceutically acceptable mode of administration can be used, including solid, semi-solid or liquid dosage forms, such as, for example, tablets, suppositories, pills, capsules, powders, liquids, suspensions, or the like, in one embodiment in unit dosage forms suitable for single administration of precise dosages, or in sustained or controlled release dosage forms for the prolonged administration of the compound at a predetermined rate. The compositions will typically include a conventional pharmaceutical carrier or excipient and an active compound or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dose for oral, parenteral and otherwise systemic routes of administration is in the range of 0.01-2000 mg/kg/day. In one embodiment, the dosage is from 0.1-100 mg/kg/day. For an average 70 kg human, this would amount to 0.7-1400 mg per day, or 7-700 mg/day.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active compounds or their salts) in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1%-95% active ingredient, in one embodiment 2-50%, in another embodiment 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

A more recently devised approach for parenteral administration employs implantation of a slow-release or sustained-release system, such that a constant level of dosage is maintained See, e.g., U.S. Pat. No. 3,710,795.

The percentage of active compound contained in such parental composition is highly dependent on the specific nature thereof, as well as the activity of the compound and the needs of the subject. However, percentages of active ingredient of 0.1% to 20% in solution are employable, and will be higher if the composition is a solid which will be subsequently diluted to the above percentages. In one embodiment, the composition will comprise 0.2-10% of the active agent in solution.

In applying the compounds of the invention to treatment of diseases or disorders of the eye, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.1% to 10%, in another embodiment 0.5% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the, range of pH 6-8. Typical preservatives are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8-8.0, making a final volume adjustment with additional water, and sterilizing the preparation using methods known to those in the art.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active components may be formulated into a gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see, e.g., Remington's Pharmaceutical Sciences, Mack Publishing Company, Easton, Pa., 16th Edition, 1980.

In one embodiment, the compositions of the present invention further comprise one or more additional pharmaceutical agents. In one embodiment, the one or more additional pharmaceutical agent is an anti-infective agent.

The term "anti-infective agents" is used throughout the specification to describe additional biologically active agents which can kill or inhibit the growth of certain other harmful or pathogenic organisms, including, but not limited to bacteria, yeast, viruses, protozoa or parasites and which can be administered to living organisms, especially animals such as mammals, particularly humans. The additional anti-infective agents includes but is not limited to antibacterial and antiviral agents. Antibacterial agents include, but are not limited to quinolones, such as ciprofloxicin, norfloxacin, ofloxacin, moxifloxacin, gatifloxacin, levofloxacin, lomefloxacin, sparfloxacin, cinoxacin, trovafloxacin, mesylate; tetracyclines particularly doxycycline and minocycline, oxytetracycline, demeclocycline, methacycline; isoniazid; penicillins, particularly penicillin g, penicillin v, penicillinase-resistant penicillins, isoxazolyl penicillins, amino penicillins, ureidopenicillins; cephalosporins; cephamycins such as cefoxitin, cefotetan, monobactams, aztreonam, loracarbef; carbapapenems such as imipenem, meropenem; β-lactamase inhibitors such as clavulanate, sulfactam, tazobactam; aminoglyclosides such as amikacin, streptomycin, gentamicin, tobramycin, netilmicin, kanamycin, macrolides such as erythromycin, rifampin, clarithromycin, azithromycin, dirithromycin, lincosamides such as lincomycin and clindamycin, glycopeptides such as vancomycin, teicoplanin, others chloramphenicol, trimethoprine/sulfamethoxazole, nitrofurantoin, oxazolidinone such as linezolid, streptogranin such as dalfopristin/quinupristin. Antiviral agents include but are not limited to zidovudine, acyclovir, ganciclovir, vidarabine, idoxuridine, trifluridine, an interferon (e.g., interferon alpha-2a or interferon alpha-2b) and ribavirin.

Determination of compatibilities of the above listed agents and other ant infective agents with, and the amounts to be utilized in, compositions of the present invention are within the purview of the ordinarily skilled artisan to determine given the teachings of this invention. The physician can determine the amount of anti-infective agent to be administered based on the subject's age, condition, and the type and severity of infection.

The therapeutic properties of many compositions of the present invention can be dramatically improved by the intravenous administration of the agent in a liposomally encapsulated form (See, for example, Shek and Barber (1986)). Toxicity can be reduced, in comparison to the free form of the anti-infective agent, meaning that a higher dose of the liposomally encapsulated anti-infective agent can safely be administered (see, for example, Lopez-Berestein, et al. (1985) J. Infect. Dis., 151:704; and Rahman, et al. (1980) Cancer Res., 40:1532). Benefits obtained from liposomal encapsulation likely result from the altered pharmacokinetics and biodistribution of the entrapped ant infective agent. A number of methods are presently available for "charging" liposomes with bioactive agents (see, for example, Rahman et al., U.S. Pat. No. 3,993,754; Sears, U.S. Pat. No. 4,145,410; Papahadjopoulos, et al., U.S. Pat. No. 4,235,871; Lenk et al., U.S. Pat. No. 4,522,803; and Fountain et al., U.S. Pat. No. 4,588,578). Ionizable bioactive agents have been shown to accumulate in liposomes in response to an imposed proton or ionic gradient (see, Bally et al., U.S. Pat. No. 5,077,056; Mayer, et al. (1986); Mayer, et al. (1988); and Bally, et al. (1988)). Liposomal encapsulation could potentially provide numerous beneficial effects for a wide variety of bioactive agents and a high bioactive agent to lipid ratio should prove important in realizing the potential of liposomally encapsulated agents.

The inhalator can be an aerosolizer, a nebulizer or a powder-administering device. It can deliver multiple doses or a single dose. A metered dose inhaler (MDI) can be used or a dry power inhaler can be employed as the inhalator. Ultrasonic, electrical, pneumatic, hydrostatic or mechanical forces such as (compressed air, or by other gases) can drive the device. The inhalation anti-infective agent delivery system can resuspend particles, or generate aerosol particles.

The inhalator can be a nebulizer, which will deliver fine mists of either liquids, suspensions or dispersions for inhalation. The devices can be mechanical powder devices which disperse fine powder into a finer mist using leverage or piezoelectric charges in combination with suitably manufactured porous filter discs, or as formulations that do not aggregate in the dose chamber. Propellants can be used to spray a fine mist of the product such as fluorochlorocarbons, fluorocarbons, nitrogen, carbon dioxide, or other compressed gases.

A nebulizer type inhalation delivery device can contain the compositions of the present invention as a solution, usually aqueous, or a suspension. In generating the nebulized spray of the compositions for inhalation, the nebulizer type delivery device can be driven ultrasonically, by compressed air, by other gases, electronically or mechanically. The ultrasonic nebulizer device generally works by imposing a rapidly oscillating waveform onto the liquid film of the formulation via an electrochemical vibrating surface. At a given amplitude the waveform becomes unstable, disintegrates the liquids film, and produces small droplets of the formulations.

A metered dose inhalator (MDI) can be employed as the inhalation delivery device of the inhalation system. This device is pressurized and its basic structure consists of a metering valve, an actuator and a container. A propellant is used to discharge the formulation from the device. The device of the inhalation system can deliver a single dose via, e.g., a blister pack, or it can be multi dose in design. The pressurized metered dose inhalator of the inhalation system can be breath actuated to deliver an accurate dose of the formulation. To insure accuracy of dosing, the delivery of the formulation can be programmed via a microprocessor to occur at a certain point in the inhalation cycle. The MDI can be portable and hand held.

A dry powder inhalator (DPI) can be used as the inhalation delivery device of the inhalation system. This device's basic design consists of a metering system, a powdered composition and a method to disperse the composition. Forces like rotation and vibration can be used to disperse the composition. The metering and dispersion systems can be mechanically or electrically driven and can be microprocessor programmable. The device can be portable and hand held. The inhalator can be multi or single dose in design and use such options as hard gelatin capsules, and blister packages for accurate unit doses. The composition can be dispersed from the device by passive inhalation; i.e., the patient's own inspiratory effort, or an active dispersion system can be employed. The dry powder of the composition can be sized via processes such as jet milling, spray dying and supercritical fluid manufacture. Acceptable excipients such as the sugars mannitol and maltose can be used in the preparation of the powdered formulations.

The anti-infective agent formulation of the present invention can contain more than one anti-infective agent (e.g., two anti-infective agents for a synergistic effect).

One skilled in this art will recognize that the above description is illustrative rather than exhaustive. Indeed, many additional formulations techniques and pharmaceutically-acceptable excipients and carrier solutions are well-known to those skilled in the art, as is the development of suitable dosing and treatment regimens for using the particular compositions described herein in a variety of treatment regimens.

Unless defined otherwise, all technical and scientific terms used herein have the same meaning as commonly understood by one of ordinary skill in the art to which this invention belongs. All publications mentioned are incorporated herein by reference. Unless mentioned otherwise, the techniques employed or contemplated herein are standard methodologies well known to one of ordinary skill in the art. The materials, methods, and examples are illustrative only and not limiting.

Experimental Procedures:

Anti-*Pneumocystis* Activities.

The structure-activity relationships for the piperazine-linked bisbenzamidines and the toxicities of each compound in three different mammalian cell lines are shown in the following tables. Compounds are ranked in order of the lowest concentration necessary to reduce the ATP content of *Pneumocystis* populations by 50% (i.e., the $IC_{50}$) compared to untreated control populations. Note that the $IC_{50}$ values are expressed on a microgram per milliliter and micromolar basis. The activity level is expressed on a scale (from highly active to no activity) modified from previous studies (Cushion, M. T., et al., 1997, Antomicrob. Agents Chemother., vol. 41, pp. 379-384; Walzer et al., 2001, Antomicrob. Agents Chemother., vol. 45, pp. 3234-3237). At the time the scale was established, no compounds were effective below an $IC_{50}$ of 0.012 µg/ml (e.g., potassium cyanide); thus, <0.100 µg/ml was set as the highest level of activity and given a semi-qualitative assessment as "very marked." In the present study, we identified four compounds with $IC_{50}$ values that were reduced in concentration by a log or more from the very-marked ranking. To differentiate this activity, a rank of highly active was assigned and defined as an $IC_{50}$ of <0.010 µg/ml.

The activity of most of the compounds fell in the "marked" category of activity. This level of activity was reported for both of the most clinically efficacious anti-*Pneumocystis* treatments, TMP-SMZ and pentamidine isethionate, with $IC_{50}$ values of 0.104 µg/ml (8) and 0.300 µg/ml, respectively. In this series of piperazine-linked bisbenzamidines, the trend of decreased activity associated with alkyl chains shorter than four carbons and longer than seven carbons is readily apparent. A reduction in carbon chain length to two and three carbons resulted in $IC_{50}$ values of 0.542 µg/ml (compound 16 [marked activity]) and 1.60 µg/ml (compound 22 [moderate activity]), whereas a single carbon chain (compound 21) or lack of an alkyl group (compound 19) resulted in moderate activity at $IC_{50}$'s of 1.53 and 1.03 µg/ml, respectively. Increases of alkyl chain length to 8, 9, 10, and 12 carbons resulted in marked activity. A benzyl ring substituent analog also showed marked activity. When both the amidinium nitrogens are part of a five- or six-membered cyclic system, the activities were either marked or moderate. Except the hydroxylamine 26 and 27 the carboxhydrazide, which were characterized by a moderate activity, the other 1,4-diarylpiperazines that were not substituted by terminal amidines moieties appeared to be devoid of activity against *Pneumocystis*.

Toxicity

Two transformed cell lines derived from two different organ systems and a primary cell line were chosen for evaluation of the relative toxicity of each compound. The A549 cell line is an epithelial lung cell line derived from a human carcinoma and has been used for this purpose in previous studies (39). The Hep-G2 cell line is an epithelial cell line derived from a human hepatocellular carcinoma, and WI-38 is a human diploid cell line derived from normal embryonic (3 months of gestation) lung tissue.

Testing in all three cell lines was conducted with compounds that showed the most promise for in vivo evaluation, i.e., those that had marked or better anti-*Pneumocystis* activity. Generally, the toxicity results for a given compound were similar for all three lines. There were only three cases in which a compound was toxic in one or two cell lines and not in the other. These included compound 5, which showed toxicity in the Hep-G2 line at 75 times the $IC_{50}$; compound 10, which was toxic to the A549 line at 2,560 times the $IC_{50}$; and compound 15, which was toxic to the Hep-G2 and WI-38 cell lines but not the A549 line at 46 and 8 times the $IC_{50}$ value. Remarkably, all four of the highly active compounds showed no toxicity in any cell line at 100 times the anti-*Pneumocystis* IC50. This lack of toxicity was also apparent in the next level of activity. Only one of the four compounds with very-marked activity (compound 5) showed slight toxicity in the Hep-G2 line at 75 times the $IC_{50}$ without toxicity in the other two cell lines. As the anti-*Pneumocystis* activity decreased, the number of compounds exhibiting toxicity increased. Six of eleven compounds with marked activity, including pentamidine, had toxicity in one or more of the cell lines, and four of the nine compounds with moderate activity showed toxicity. The moderately active compounds were usually screened only in the A549 cell line, since compounds with this level of activity were not selected for further study in animal models. For the same reason, compounds with slight or no activity were not tested in the cell line assays.

BRIEF DESCRIPTION OF TABLES

Table 1 deals with the reference known compound (Pentamidine)

Table 2 deals with compounds defined as in Group I

Table 3 deals with analogs of compounds defined in Group I

Table 4a deals with compounds defined as in Group I

Table 4b deals with compounds related to Group I

Tables 5, 6, 7, and 8 deal with compounds of Group II

TABLE 1

$IC_{50}$s of pentamidine analogues for *Pneumocystis* and A549 lung epithelial cells after 48 hours exposure. Pentamidine is the reference compound.

| Compound | Anti-*P. carinii* Activity | *P. carinii* $IC_{50}$ (µg/ml) | A549 $IC_{50}$ (µg/ml) | DNA Binding $\Delta T_m$ (°C.) Calf thymus | Poly (dA-dT) |
|---|---|---|---|---|---|
| Pentamidine | marked | 0.300 | — | 11.1 | 20.6 |

TABLE 2

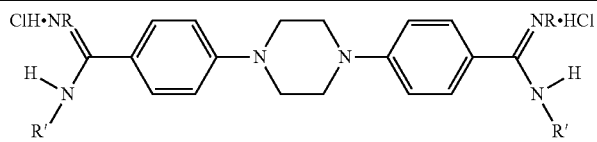

|   |   |   |  | A549 | DNA Binding ΔT$_m$ (° C.) | |
|---|---|---|---|---|---|---|
| R | R' | Anti-Pneumocystis Activity | Pneumocystis IC$_{50}$ (μg/ml) | IC$_{50}$ (μg/ml) | Calf thymus | Poly (dA-dT) |

R' =

A: isopropyl (CH(CH$_3$)$_2$)

B: cyclohexyl

C: —H$_2$C—phenyl (benzyl)

D: cyclopentyl

E: —CH$_3$

F: cyclopropyl

| R | R' | Anti-Pneumocystis Activity | Pneumocystis IC$_{50}$ (μg/ml) | A549 IC$_{50}$ (μg/ml) | Calf thymus | Poly (dA-dT) |
|---|---|---|---|---|---|---|
| H | —C$_4$H$_9$ | Very marked | 0.046 | >4.63 | 15.2 | 23.9 |
| H | A | Marked | 0.116 | >11.6 | 15.5 | 23.6 |
| H | B | Marked | 0.139 | 356.4 | 18.0 | 25.1 |
| H | C | Marked | 0.226 | >22.6 | 14.0 | 23.0 |
| H | H | Moderate | 1.03 | 163.3 | 17.0 | 23.8 |
| H | D | Moderate | 1.53 | >153 | 15.2 | 22.2 |
| H | —C$_3$H$_7$ | Moderate | 1.6 | 1,070 | 17.0 | 26.0 |
| H | E | Moderate | 2.5 | >100 | 14.5 | 23.9 |
| H | F | Moderate | 3.01 | >60.2 | 14.9 | 22.5 |
| H | —OH | Moderate | 3.3 | — | 0.8 | — |

R' =

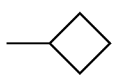

A: cyclobutyl

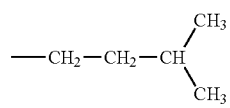

B: —CH$_2$—CH$_2$—CH(CH$_3$)$_2$

TABLE 2-continued

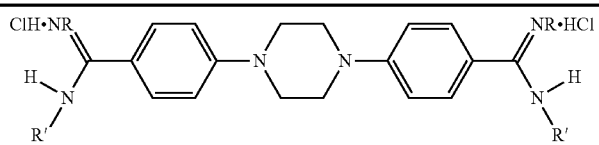

|  |  |  |  | A549 | DNA Binding $\Delta T_m$ (° C.) | |
|---|---|---|---|---|---|---|
| R | R' | Anti-Pneumocystis Activity | Pneumocystis IC$_{50}$ (μg/ml) | IC$_{50}$ (μg/ml) | Calf thymus | Poly (dA-dT) |

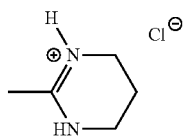

C

—C$_{H_2}$—CH—C$_{H_2}$—CH$_3$
       |
       CH$_3$

D

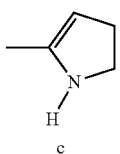

E

| H | —C$_2$H$_5$ | Marked | | | 15.3 | 18.6 |
|---|---|---|---|---|---|---|
| H | A | Very Marked | | | 16.4 | — |
| H | —C$_5$H$_{11}$ | Highly Active | | | 16.9 | 22.5 |
| H | B | Highly Active | | | 15.3 | 21.8 |
| H | C | Very Marked | | | 12.9 | 16.0 |
| H | —C$_6$H$_{13}$ | Highly Active | | | 10.7 | 10.1 |
| H | —C$_7$H$_{15}$ | Very Marked | | | 8.7 | 8.5 |
| H | D | Highly Active | | | 15.6 | 18.7 |
| H | —C$_8$H$_{17}$ | Marked | | | 4.2 | — |
| H | E | Marked | | | 12.6 | 15.7 |
| H | —C$_9$H$_{19}$ | Marked | | | 1.3 | 2.7 |
| H | —C$_{10}$H$_{21}$ | Marked | | | 1.3 | — |
| H | —C$_{12}$H$_{25}$ | Marked | | | 0.6 | 0.0 |

R, R' =

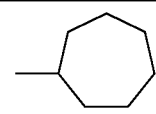

a

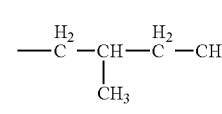

b

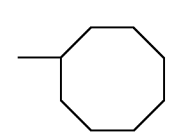

c

| See above | | Marked | 0.177 | — | 15.0 | 19.4 |
|---|---|---|---|---|---|---|
| See above | | Marked | 0.711 | >71 | 0.1 | 2.0 |
| See above | | Moderate | 1.3 | >130 | 15.0 | 19.4 |

TABLE 2-continued

[Structure: ClH·NR(H)(R'N)C-C6H4-N(piperazine)N-C6H4-C(NR·HCl)(NHR')]

| R | R' | Anti-Pneumocystis Activity | Pneumocystis IC$_{50}$ (μg/ml) | A549 IC$_{50}$ (μg/ml) | DNA Binding ΔT$_m$ (°C.) Calf thymus | DNA Binding ΔT$_m$ (°C.) Poly (dA-dT) |
|---|---|---|---|---|---|---|
| See above | | Moderate | 1.44 | >100 | 20.4 / 12.2 | 29.1 / 17.9 |

TABLE 3

[Structure: R-C6H4-N(piperazine)N-C6H4-R]

| R | Groups |
|---|---|
| A | —C(=O)—N(H)—NH$_2$ |
| B | —C(=O)—OC$_2$H$_5$ |
| C | 2-methyl-1,3-diphenyl-imidazolidine |
| D | —C(H)=N—N(H)—phenyl |
| E | 2-methyl-1,3-dioxolane |
| F | 1,3-dimethyl-2-methyl-imidazolidine |
| G | —CHO |
| H | —C(=O)—CH$_3$ |

| R | Anti-Pneumocystis Activity | Pneumocystis IC$_{50}$ (μg/ml) | A549 IC$_{50}$ (μg/ml) | DNA Binding ΔT$_m$ (°C.) Calf thymus | DNA Binding ΔT$_m$ (°C.) Poly (dA-dT) |
|---|---|---|---|---|---|
| A | Moderate | 6.02 | 3,070 | 0.1 | 0.0 |
| —NO$_2$ | Slight | 34.1 | | 0.1 | 0.0 |
| —CN | No activity | 97.2 | | 0.1 | −0.3 |
| B | No activity | >100 | | −0.2 | 0.0 |
| C | No activity | >100 | | 2.4 | 1.8 |
| D | No activity | >100 | | −1.2 | 0.0 |
| E | No activity | >100 | | −1.2 | 0.1 |
| F | No activity | >100 | | 0.6 | 0.0 |
| G | No activity | >100 | | −0.2 | 0.0 |
| H | No activity | >100 | | 0.1 | 0.0 |

TABLE 4a

[Structure: ClH·RN(H)(R'N)C-C6H4-N(homopiperazine)N-C6H4-C(NR·HCl)(NHR')]

A: 2-methyl-1,4,5,6-tetrahydropyrimidine

B: cyclopropyl

DNA Binding

TABLE 4a-continued

| R | R' | Anti-Pneumocystis Activity | Pneumocystis IC$_{50}$ (μg/ml) | A549 IC$_{50}$ (μg/ml) | ΔT$_m$ (°C.) Calf thymus | ΔT$_m$ (°C.) Poly (dA-dT) |
|---|---|---|---|---|---|---|
| H | —C$_4$H$_9$ | Marked | 0.186 | >18.6 | 11.8 | 13.3 |
| H | H | Marked | 0.835 | >83.5 | 15.0 | 23.1 |
| A, A | | Moderate | 2.18 | 173.7 | 15.5 | 21.3 |
| H | B | | | | 15.3 | 23.6 |

TABLE 4b

Amidine (-containing) group — Aromatic group — LINKER — Aromatic group — Aminide (-containing) group

| Amidine-containing group | Aromatic group | LINKER | Anti-P. carinii Activity | P. carinii IC$_{50}$ (μg/ml) | A549 IC$_{50}$ (μg/ml) | Calf thymus | Poly (dA-dT) |
|---|---|---|---|---|---|---|---|
| 2-methyl-imidazoline·HCl | phenyl | piperidinyl-CH$_2$ | Moderate | 1.23 | 27.7 | 9.9 | 14.1 |
| 2-methyl-imidazoline·HCl | phenyl | piperidinylidene-CH | Moderate | 1.25 | 47.6 | 12.0 | 15.0 |

TABLE 5

Structure: RN(H)(R'N(H))C—C$_6$H$_4$—NH—C(O)—CHAIN—C(O)—NH—C$_6$H$_4$—C(NR)(N(H)R')

| CHAIN | R | R' | Anti-P. carinii Activity | P. carinii IC$_{50}$ (μg/ml) | A549 IC$_{50}$ (μg/ml) | Calf thymus | Poly (dA-dT) |
|---|---|---|---|---|---|---|---|
| —(CH$_2$)$_4$ | H | H | Very marked | 0.00087 | — | 8.7 | 14.4 |
| —(CH$_2$)$_3$ | H | H | Very marked | 0.0013 | >0.130 | 4.8 | 4.5 |
| | | | | | | 5.6 | 11.4 |
| m-phenylene | H | H | marked | 0.578 | >57.8 | 8.0 | 9.9 |
| m-phenylene | H | OH | No activity | >100 | — | 0.6 | 0.1 |
| p-phenylene | H | H | Slight | 10.8 | >100.8 | 9.7 | 7.7 |
| p-phenylene | H | OH | No activity | >100 | — | 0.6 | 0.0 |
| cyclopropane-1,2-diyl | H | H | Moderate | 2.3 | >230 | 7.1 | 11.1 |

TABLE 5-continued

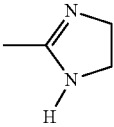

| CHAIN | R | R' | Anti-P. carinii Activity | P. carinii IC$_{50}$ (μg/ml) | A549 IC$_{50}$ (μg/ml) | DNA Binding ΔT$_m$ (°C.) Calf thymus | DNA Binding ΔT$_m$ (°C.) Poly (dA-dT) |
|---|---|---|---|---|---|---|---|
| 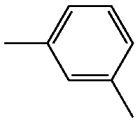 | | | Moderate | 8.2 | 284.1 | 6.0 | 9.6 |

TABLE 6

| CHAIN | R | R' | Anti-P. carinii Activity | P. carinii IC$_{50}$ (μg/ml) | A549 IC$_{50}$ (μg/ml) | DNA Binding ΔT$_m$ (°C.) Calf thymus | DNA Binding ΔT$_m$ (°C.) Poly (dA-dT) |
|---|---|---|---|---|---|---|---|
| *meta-phenyl* | H | OH | Slight | 15.1 | — | −0.3 | 0.1 |
| *para-phenyl* | H | OH | No activity | 83.3 | — | 0.4 | 0.1 |

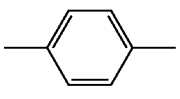

| CHAIN | R | R' | Anti-P. carinii Activity | P. carinii IC$_{50}$ (μg/ml) | A549 IC$_{50}$ (μg/ml) | DNA Binding ΔT$_m$ (°C.) Calf thymus | DNA Binding ΔT$_m$ (°C.) Poly (dA-dT) |
|---|---|---|---|---|---|---|---|
| *para-phenyl* | H | H | moderate | 6.38 | — | 9.9 | — |

TABLE 8a

| CHAIN | R | R' | Anti- P. carinii Activity | P. carinii IC$_{50}$ (μg/ml) | A549 IC$_{50}$ (μg/ml) | DNA Binding Δ Tn, (° C) Calf thymus | DNA Binding Δ Tn, (° C) Poly (dA-dT) |
|---|---|---|---|---|---|---|---|
| —H$_2$C—⟨p-phenylene⟩—CH$_2$— | H | H | Marked | 0.583 | — | 12.5 | 18.0 |
| ⟨o-xylylene⟩ | H | H | Marked | 0.786 | — | −0.2 | −0.1 |
| ⟨m-xylylene⟩ | H | H | Moderate | 1.18 | — | 14.0 | |

TABLE 8b

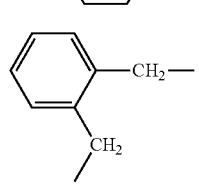

| CHAIN | R | R' | Anti- P. carinii Activity | P. carinii IC$_{50}$ (μg/ml) | A549 IC$_{50}$ (μg/ml) | DNA Binding Δ T$_m$ (° C.) Calf thymus | DNA Binding Δ T$_m$ (° C.) Poly (dA-dT) |
|---|---|---|---|---|---|---|---|
| ⟨o-phenylenedioxy⟩ | H | H | Marked | 0.627 | — | 0.1 | −0.1 |

What is claimed is:

1. A bis-benzamidine of the following structure

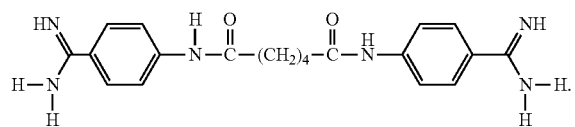

2. A bis-benzamidine of the following structure:

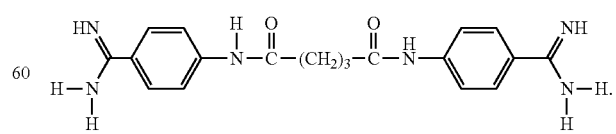

* * * * *